United States Patent
Cohen et al.

(10) Patent No.: US 10,899,733 B2
(45) Date of Patent: Jan. 26, 2021

(54) INHIBITORS OF PARPS THAT CATALYZE MONO-ADP-RIBOSYLATION

(71) Applicant: OREGON HEALTH & SCIENCE UNIVERSITY, Portland, OR (US)

(72) Inventors: Michael Cohen, Portland, OR (US); Rory Morgan, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 16/109,643

(22) Filed: Aug. 22, 2018

(65) Prior Publication Data

US 2019/0062302 A1 Feb. 28, 2019

Related U.S. Application Data

(60) Provisional application No. 62/549,352, filed on Aug. 23, 2017.

(51) Int. Cl.
| | | |
|---|---|---|
| *C07D 401/04* | (2006.01) | |
| *C07D 217/24* | (2006.01) | |
| *C07D 487/04* | (2006.01) | |

(52) U.S. Cl.
CPC ......... *C07D 401/04* (2013.01); *C07D 217/24* (2013.01); *C07D 487/04* (2013.01)

(58) Field of Classification Search
CPC ... C07D 217/24; C07D 401/04; C07D 487/04
See application file for complete search history.

(56) References Cited

U.S. PATENT DOCUMENTS

| | | |
|---|---|---|
| 6,664,269 B2 | 12/2003 | Martin et al. |
| 8,592,416 B2 | 11/2013 | Papeo et al. |
| 8,969,565 B2 | 3/2015 | Bi et al. |
| 9,376,433 B2 | 6/2016 | Dorsch et al. |
| 2004/0176361 A1 | 9/2004 | Fujio et al. |
| 2004/0224959 A1 | 11/2004 | Ohkura et al. |
| 2005/0256124 A1 | 11/2005 | Goodfellow et al. |
| 2011/0178041 A1 | 7/2011 | Kohno et al. |
| 2014/0051681 A1 | 2/2014 | Augeri et al. |
| 2014/0348857 A1 | 11/2014 | Chang et al. |
| 2018/0111916 A1 | 4/2018 | Gray et al. |
| 2019/0152941 A1 | 5/2019 | Gao et al. |

OTHER PUBLICATIONS

Ortega, Bioorganic & Med Chem Lett, vol. 21, 2670-2674. 2011. (Year: 2011).*
Sivaprakasam, Blood & Med CHem Lett, vol. 25, 1856-1863, 2015. (Year: 2015).*
Mukherjee, J Chem Info Model, vol. 57, 2152-2160, 2017. (Year: 2017).*
Johnson, J comput Aided Mol Des, vol. 25, 689-698, 2011. (Year: 2011).*
Chaweewannakorn et al., Ameloblastin and enamelin prevent osteoclast formation by suppressing RANKL expression via MAPK signaling pathway, Biochemical and Biophysical Research Communications 485 (2017) 621-626.
Ekblad et al., Towards small molecule inhibitors of mono-ADP-ribosyltransferases, Eur J Med Chem 95 (2015) 546-551.
Gupte et al., PARPs and ADP-ribosylation: recent advances linking molecular functions to biological outcomes, Genes Dev. 2017 31: 101-126.
Jwa et al., PARP16 is a tail-anchored endoplasmic reticulum protein required for the PERK- and IRE1-mediated unfolded protein response, Nature Cell Biology, vol. 14, No. 11, Nov. 2012, pp. 1223-1230, plus 7 pages figures.
Kurouchi et al., Protonation Switching to the Least-Basic Heteroatom of Carbamate through Cationic Hydrogen Bonding Promotes the Formation of Isocyanate Cations, Chem Eur J, 2014, 20, 8682-8690.
Morgan et al., Selective inhibition of PARP10 using a chemical genetics strategy, Biorganic & Medicinal Chemistry Letters, 25 (2015) 4770-4773.
Mukherjee et al., Kinase Crystal Miner: A Powerful Approach to Repurposing 3D Hinge Binding Fragments and Its Application to Finding Novel Bruton Tyrosine Kinase Inhibitors, J Chem Inform Model., 2017, 57, 2152-2160.
Ortega et al., Aromatic ring functionalization of benzolactam derivatives: New potent dopamine D3 receptor ligands, Bioorganic & Medicinal Chemistry Letters 21 (2011) 2670-2674.
Peng et al., Small Molecule Microarray Based Discovery of PARP14 Inhibitors, Angew. Chem. Int. Ed. 2017, 56, 248-253.
Pinto et al., Comparative Structural Analysis of the Putative Mono-ADP-Ribosyltransferases of the ARTD/PARP FamilyCurrent Topics in Microbiology and Immunology (2015) 384: 153-166.
Spicer et al., Exploration of a Series of 5-Arylidene-2-thioxoimidazollidine-4-ones as Inhibitors of the Cytolytic Protein Perforin, J. Med. Chem. 2013, 56, 9542-9555.
Suto et al., Dihydroisoquinolinones: the design and synthesis of a new series of potent inhibitors of poly(ADP-ribose) polymerase*, Anti-Cancer Drug Design (1991), 7, 107-117.
Tangallapally et al., Synthesis of new and potent analogues of anti-tuberculosis agent 5-nitro-furan-2-carboxylic acid 4-(4-benzyl-piperazin-1-yl)-benzylamide with improved bioavailability, / Bioorg. Med. Chem. Lett. 16 (2006) 2584-2589.
Thorsell et al., Structural Basis for Potency and Promiscuity in Poly(ADP-ribose) Polymerase (PARP) and Tankyrase Inhibitors, J. Med. Chem. 2017, 60, 1262-1271.

(Continued)

*Primary Examiner* — D Margaret M Seaman (57) ABSTRACT

Provided herein are compounds of Formula I, or a pharmaceutically acceptable salt thereof:

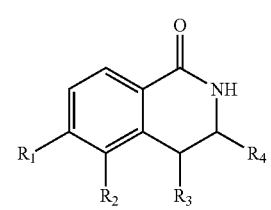

Formula I which are useful as PARP inhibitors, as well as pharmaceutical compositions comprising them and methods for their use in treating disorders.

10 Claims, 2 Drawing Sheets

(56) References Cited

OTHER PUBLICATIONS

Upton et al., Design and synthesis of potent inhibitors of the mono(ADP-ribosyl)transferase, PARP14, Bioorganic & Medicinal Chemistry Letters 27 (2017) 2907-2911.
Venkannagari et al., Small-Molecule Chemical Probe Rescues Cells from Mono-ADP-Ribosyltransferase ARTD10/PARP10-Induced Apoptosis and Sensitizes Cancer Cells to DNA Damage, Cell Chemical Biology 23, 2016, 1251-1260.
Venkannagari et al., Activity-based assay for human mono-ADP-ribosyltransferases ARTD7/PARP15 and ARTD10/PARP10 aimed at screening and profiling inhibitors, European Journal of Pharmaceutical Sciences 49 (2013) 148-156.
Verheugd et al., Regulation of NF-kB signalling by the mono-ADP-ribosyltransferase ARTD10, Nature Communications, 2013; 4:1683.
Vyas et al., Family-wide analysis of poly(ADP-ribose) polymerase activity, 2014, 5, 4426.
Wang et al. Epigallocatechin-3-gallate enhances ER stress-induced cancer cell apoptosis by directly targeting PARP16 activity, Cell Death Discovery (2017) 3, 17034; doi:10.1038/cddiscovery.2017.34.
Wissel et al., A structure-activity relationship study of ABCC2 inhibitors, European Journal of Pharmaceutical Sciences, 103 (2017) 60-69.
Yoneyama-Hirazane et al., Identification of PARP14 inhibitors using novel methods for detecting auto-ribosylation, Biochemical and Biophysical Research Communications 486 (2017) 626-631.
Pellicciari et al., On the Way to Selective PARP-2 Inhibitors. Design, Synthesis, and Preliminary Evaluation of a Series of Isoquinolinone Derivatives, ChemMedChem 2008, 3, 914-923.
Watson et al., Synthesis of 3-Substituted Benzamides and 5-Substituted Isoquinolin-1(2H)-ones and Preliminary Evaluation as Inhibitors of Poly(ADP-ribose)polymerase (PARP), Bioorganic & Medicinal Chemistry 6 (1998) 721-734.

* cited by examiner

INHIBITORS OF PARPS THAT CATALYZE MONO-ADP-RIBOSYLATION

Provided are novel compounds useful as selective inhibitors of PARP10 and PARP16 useful in the treatment of cancer and protein folding disorders.

BACKGROUND OF THE INVENTION

Many members of the poly(ADP-ribose polymerase family (ParpS), both poly-(ADP-ribose) polymerases and mono-(ADP-ribosyl)transferases, are implicated in DNA damage rep-air and genomic integrity. PARP10 and PARP16 been shown to play a role in chromatin remodeling and DNA repair, making selective inhibitors of both of interest in drug development and as research tools.

The poly(ADP-ribose) polymerase (PARP) family of enzymes (17 in humans; also known as ADP-ribosyltransferases or ARTDs) catalyze the transfer of ADP-ribose onto amino acids of protein substrates from donor nicotinamide adenine dinucleotide ($NAD^+$) in a process known as ADP-ribosylation (ADPr). In recent years, PARPs have emerged as major regulators of cellular processes ranging from chromatin regulation, transcription, RNA biology, DNA repair, stress responses, and metabolism. {Gupte, R., Liu, Z., Kraus, W. L., 2017. PARPs and ADP-ribosylation: recent advances linking molecular functions to biological outcomes. Genes Dev. 31, 101-126. doi:10.1101/gad.291518.116} PARPs can be divided into two subfamilies based on their differences in catalytic activity: those that catalyze poly-ADPr (PARPs 1, 2, 5a, 5b) and those that catalyze mono-ADPr (PARPs 3, 4, 6-8, 10-12, 14-16). {Vyas et al., 2014. Family-wide analysis of poly(ADP-ribose) polymerase activity. Nat. Commun. 5, 4426} Much progress has been made in understanding the functions of PARPs with poly-ADPr activity such as PARP1, PARP2, and the tankyrases (PARPs 5a, b) due to the development of selective inhibitors for these PARPs. However, a comprehensive understanding of the functions of the remaining PARPs that catalyze mono-ADPr has been hindered due to a lack of selective inhibitors. To date, there have been only a few reports of inhibitor development directed toward PARPs with mono-ADPr activity, but many of these reported inhibitors are not selective or have only been profiled against a select number of PARP family members. {Yoneyama-Hirozane et al., 2017; Identification of PARP14 inhibitors using novel methods for detecting auto-ribosylation. Biochem. Biophys. Res. Commun. 486, 626-631; Ekblad et al., 2015. Towards small molecule inhibitors of mono-ADP-ribosyltransferases. Eur. J. Med. Chem. 95, 546-551; Peng et al., 2017. Small molecule microarray based discovery of PARP14 inhibitors. Angew. Chem. Int. Ed. Engl. 56, 248-253; and Upton et al., 2017. Design and synthesis of potent inhibitors of the mono(ADP-ribosyl)transferase, PARP14. Bioorg. Med. Chem. Lett. 27, 2907-2911}.

Figure 1A:
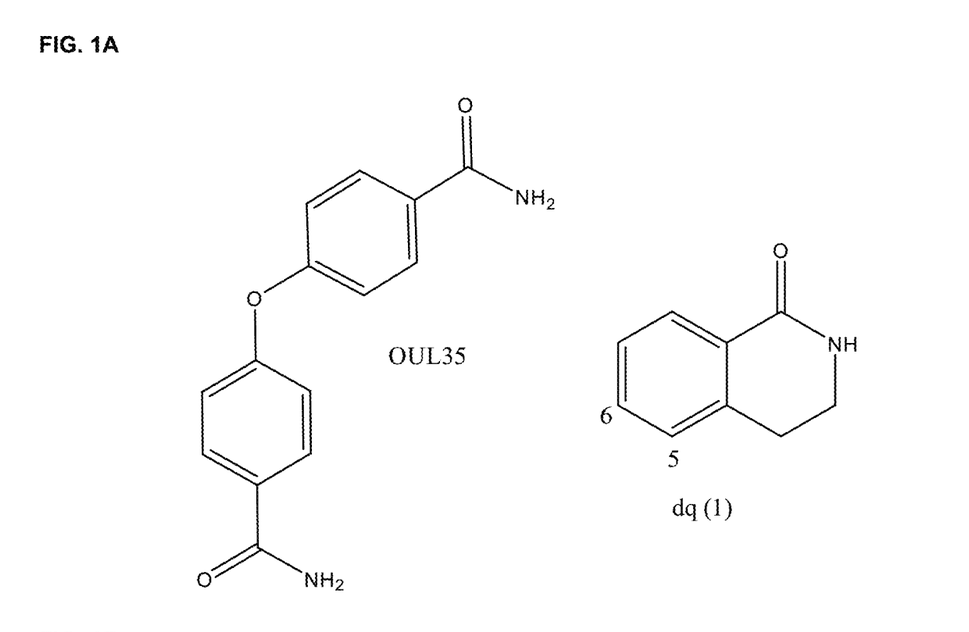
FIG. 1A provides chemical structures of PARP10-selective inhibitor OUL35 and 3,4-dihydroisoquinolin-1(2H)-one.

PARP10 (ARTD10) is a member of the subclass of PARPs that catalyze mono-APDr and has been implicated in various biological pathways involving DNA repair {Nicolae: 2014e1} and inflammation {Verheugd et al., 2013. Regulation of NF-κB signaling by the mono-ADP-ribosyltransferase ARTD10. Nat. Commun. 4, 1683}, yet a clear connection of PARP catalytic activity to the regulation of these pathways is still not clear. A selective small molecule probe of PARP10 could enable detailed mechanistic studies of PARP10-mediated biology, and furthermore, validate PARP10 as a therapeutic target for diseases such as cancer. {Vyas et al., 2014, Nat. Commun. 5, 4426} A recent study described a small-molecule chemical probe known as OUL35, 4,4'-oxydibenzamide, (FIG. 1) as a potent and selective inhibitor of PARP10, exhibiting >12-fold selectivity over other PARP family members examined. {Venkannagari et al., Cell Chem. Biol., 2016, 23, pp. 1251-1260} Of the PARPs tested in the study, OUL35 was not assayed against PARP11.

ARTD10/PARP10 inhibitor OUL35 has been shown to sensitize cells to DNA damage, (Venkannagari et al., Cell Chemical Biology 23, 1251-1260. Oct. 20, 2016).

PARP16 inhibition has been associated with increasing endoplasmic reticulum (ER) stress conditions during cancer cell apoptosis. Wang et al., Cell Death Discovery, page 17034. Vol. 3, 2017. U.S. patent application Ser. No. 14/353, 940, published as US2014/0348857A1, Chang et al., discusses the use of PARP16 inhibitors in the treatment of ER stress-related conditions in human cancers and other disorders.

There remains a need for discovering compounds that can selectively inhibit each PARP enzyme, including PARP10 and PARP16.

SUMMARY OF THE INVENTION

Provided herein is a compound of Formula I, or a pharmaceutically acceptable salt thereof:

Formula I wherein:

$R_1$ is selected from the group of $C_1$-$C_6$ alkyl, $C_2$-$C_6$ alkenyl, $C_2$-$C_6$ alkynyl, —$(CH_2)_{n^1}$-phenyl, —$(CH_2)_{n^2}$-naphthalenyl, and —$(CH_2)_{n^3}$-Het, wherein Het is a 5- to 10-membered heterocyclic group having 1, 2, 3, or 4 ring nitrogen atoms; with each of the $R_1$ $C_1$-$C_6$ alkyl, $C_2$-$C_6$ alkenyl, $C_2$-$C_6$ alkynyl groups and the phenyl, naphthalenyl, and Het rings of the —$(CH_2)_{n^1}$-phenyl, —$(CH_2)_{n^2}$-naphthalenyl, and —$(CH_2)_{n^3}$-Het groups, respectively, being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl)$_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl;

$n^1$, $n^2$, and $n^3$ are integers independently selected in each instance from 0, 1, 2, and 3;

$R_2$ is selected from the group of H, halogen, $C_1$-$C_6$ alkyl, $C_2$-$C_6$ alkenyl, $C_2$-$C_6$ alkynyl, $C_1$-$C_6$ alkoxy, $NH_2$, $NH(C_1$-$C_6$ alkyl), and $N(C_1$-$C_6$ alkyl)$_2$, phenyl, —O-phenyl, benzyl, and —O-benzyl; with each of the $R_2$ $C_1$-$C_6$ alkyl, $C_2$-$C_6$ alkenyl, $C_2$-$C_6$ alkynyl groups and the rings of the phenyl, —O-phenyl, benzyl, and —O-benzyl groups being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), and $N(C_1$-$C_6$ alkyl)$_2$;

$R_3$ is selected from H, $C_1$-$C_6$ alkyl, and phenyl, with the $C_1$-$C_6$ alkyl and phenyl groups being substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), and $N(C_1$-$C_6$ alkyl$)_2$; and $R_4$ is selected from H, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl, with the alkyl chain of the —$CO_2(C_1$-$C_6$ alkyl) group and the rings of the —$CO_2$-phenyl, —$CO_2$-benzyl, —$CO_2$—$C_3$-$C_6$ cycloalkyl, and —$CO_2$—$CH_2$—$C_3$-$C_6$ cycloalkyl groups being substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), and $N(C_1$-$C_6$ alkyl$)_2$;

with the proviso that, when $R_1$ is methyl and $R_4$ is $CO_2H$, then $R_2$ is not H.

DETAILED DESCRIPTION OF THE INVENTION

Also provided is a compound of Formula II, or a pharmaceutically acceptable salt thereof:

Formula II wherein $R_1$, $R_2$, and $R_3$ are as defined for Formula I, above, and $R_5$ is selected from $R_4$ is selected from H, $C_1$-$C_6$ alkyl, phenyl, benzyl, $C_3$-$C_6$ cycloalkyl, and —$CH_2$—$C_3$-$C_6$ cycloalkyl, each of which is substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl$)_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl.

Also provided is a compound of Formula III, or a pharmaceutically acceptable salt thereof:

Formula III wherein:

$R_1$ is selected from the group of $C_1$-$C_6$ alkyl, $C_2$-$C_6$ alkenyl, $C_2$-$C_6$ alkynyl, —$(CH_2)_n^1$-phenyl, —$(CH_2)_n^2$-naphthalenyl, and —$(CH_2)_n^3$-Het, wherein Het is a 5- to 10-membered heterocyclic group having 1, 2, 3, or 4 ring nitrogen atoms; in which each of the $R_1$ $C_1$-$C_6$ alkyl, $C_2$-$C_6$ alkenyl, $C_2$-$C_6$ alkynyl groups and the phenyl, naphthalenyl, and Het rings of the —$(CH_2)_n^1$-phenyl, —$(CH_2)_n^2$-naphthalenyl, and —$(CH_2)_n^3$-Het groups, respectively, are independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl$)_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl;

$n^1$, $n^2$, and $n^3$ are integers independently selected in each instance from 0, 1, 2, and 3; and $R_2$ is selected from the group of H, halogen, $C_1$-$C_6$ alkyl, $C_2$-$C_6$ alkenyl, $C_2$-$C_6$ alkynyl, $C_1$-$C_6$ alkoxy, $NH_2$, $NH(C_1$-$C_6$ alkyl), and $N(C_1$-$C_6$ alkyl$)_2$, phenyl, —O-phenyl, benzyl, and —O-benzyl; with each of the $R_2$ $C_1$-$C_6$ alkyl, $C_2$-$C_6$ alkenyl, $C_2$-$C_6$ alkynyl groups and the rings of the phenyl, —O-phenyl, benzyl, and —O-benzyl groups each being substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), and $N(C_1$-$C_6$ alkyl$)_2$.

Further provided is a compound of Formula III, or a pharmaceutically acceptable salt thereof, wherein:

$R_1$ is selected from the group of —$(CH_2)_n^1$-phenyl, —$(CH_2)_n^2$-naphthalenyl, and —$(CH_2)_n^3$-Het, wherein Het is a 5- to 10-membered heterocyclic group having 1, 2, 3, or 4 ring nitrogen atoms; with each of the $R_1$ phenyl, naphthalenyl, and Het rings of the —$(CH_2)_n^1$-phenyl, —$(CH_2)_n^2$-naphthalenyl, and —$(CH_2)_n^3$-Het groups, respectively, being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl$)_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl;

$n^1$, $n^2$, and $n^3$ are integers independently selected in each instance from 0, 1, 2, and 3; and $R_2$ is selected from the group of H, halogen, $C_1$-$C_6$ alkyl, $C_2$-$C_6$ alkenyl, $C_2$-$C_6$ alkynyl, $C_1$-$C_6$ alkoxy, $NH_2$, $NH(C_1$-$C_6$ alkyl), and $N(C_1$-$C_6$ alkyl$)_2$, phenyl, —O-phenyl, benzyl, and —O-benzyl; with each of the $R_2$ $C_1$-$C_6$ alkyl, $C_2$-$C_6$ alkenyl, $C_2$-$C_6$ alkynyl groups and the rings of the phenyl, —O-phenyl, benzyl, and —O-benzyl groups each being substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), and $N(C_1$-$C_6$ alkyl$)_2$.

Also provided is a compound of Formula III, or a pharmaceutically acceptable salt thereof, wherein:

$R_1$ is selected from the group of —$(CH_2)_n^1$-phenyl, —$(CH_2)_n^2$-naphthalenyl, and —$(CH_2)_n^3$-Het, wherein Het is a 5- to 10-membered heterocyclic group having 1, 2, 3, or 4 ring nitrogen atoms; with each of the $R_1$ phenyl, naphthalenyl, and Het rings of the —$(CH_2)_n^1$-phenyl, —$(CH_2)_n^2$-naphthalenyl, and —$(CH_2)_n^3$-Het groups, respectively, being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl$)_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl;

$n^1$, $n^2$, and $n^3$ are integers independently selected in each instance from 0, 1, 2, and 3; and $R_2$ is selected from the group of $C_1$-$C_6$ alkyl substituted by 0, 1, 2, 3, 4, or 5 substituents selected from OH, halogen, $CF_3$, $NH_2$, $NH(C_1$-$C_6$ alkyl), and $N(C_1$-$C_6$ alkyl)$_2$.

Also provided is a compound of Formula III, or a pharmaceutically acceptable salt thereof, wherein:

$R_1$ is selected from the group of —$(CH_2)_n{}^1$-phenyl, —$(CH_2)_n{}^2$-naphthalenyl, and —$(CH_2)_n{}^3$-Het, wherein Het is a 5- to 10-membered heterocyclic group having 1, 2, 3, or 4 ring nitrogen atoms; with each of the $R_1$ phenyl, naphthalenyl, and Het rings of the —$(CH_2)_n{}^1$-phenyl, —$(CH_2)_n{}^2$-naphthalenyl, and —$(CH_2)_n{}^3$-Het groups, respectively, being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl)$_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl;

$n^1$, $n^2$, and $n^3$ are integers independently selected in each instance from 0, 1, 2, and 3; and $R_2$ is selected from the group of $C_1$-$C_3$ alkyl substituted by 0, 1, 2, 3, 4, or 5 substituents selected from OH, halogen, $CF_3$, $NH_2$, $NH(C_1$-$C_6$ alkyl), and $N(C_1$-$C_6$ alkyl)$_2$.

Further provided is a compound of Formula IV, or a pharmaceutically acceptable salt thereof:

Formula IV wherein:

$R_1$ is selected from the group of —$(CH_2)_n{}^1$-phenyl, —$(CH_2)_n{}^2$-naphthalenyl, and —$(CH_2)_n{}^3$-Het, wherein Het is a 5- to 10-membered heterocyclic group having 1, 2, 3, or 4 ring nitrogen atoms; with each of the $R_1$ phenyl, naphthalenyl, and Het rings of the —$(CH_2)_n{}^1$-phenyl, —$(CH_2)_n{}^2$-naphthalenyl, and —$(CH_2)_n{}^3$-Het groups, respectively, being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl)$_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl; and

$n^1$, $n^2$, and $n^3$ are integers independently selected in each instance from 0, 1, 2, and 3.

Additionally provided is a compound of Formula IV, or a pharmaceutically acceptable salt thereof, wherein $R_1$ is selected from the group of phenyl, naphthalenyl, and Het, wherein Het is a 5- to 10-membered heterocyclic group having 1, 2, 3, or 4 ring nitrogen atoms; with each of the $R_1$ phenyl, naphthalenyl, and Het rings being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl)$_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl.

Also provided is a compound of Formula IV, or a pharmaceutically acceptable salt thereof, wherein $R_1$ is selected from the group of phenyl, naphthalenyl, benzyl, pyridinyl, pyrrolidinyl, pyrrolyl, imidazolyl, pyrazolyl, 1,2,3-triazolyl, 1,2,4-triazolyl, tetrazolyl, piperazinyl, pyrazinyl, pyrimidinyl, pyridazinyl, 1,2,3-triazinyl, 1,2,4-triazinyl, 1,3,5-triazinyl, indolyl, purinyl, quinolinyl, isoquinolinyl, benzimidazolyl, pyrrolo[2,3-b]pyridinyl; with each of the $R_1$ rings being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl)$_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl.

Additionally provided is a compound of Formula IV, or a pharmaceutically acceptable salt thereof, wherein $R_1$ is selected from the group of phenyl, naphthalenyl, benzyl, quinolinyl, indolyl, pyridinyl, pyrrolo[2,3-b]pyridinyl; with each of the $R_1$ rings being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl)$_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl.

Also provided are compounds of Formula V:

Formula V wherein:

$R_7$ is selected from the group of H, F, Cl, $CH_3$, $CF_3$, $CO_2H$, and —$CO_2(C_1$-$C_6$ alkyl);

$X^1$ is selected from the group of CH and N; and $X^2$ is selected from the group of CH and N;

with the proviso that only one of $X^1$ and $X^2$ can be N; or a pharmaceutically acceptable salt thereof.

One embodiment comprises compounds of Formula V, or a pharmaceutically acceptable salt thereof, wherein $R_7$ is selected from the group of H, F, Cl, $CH_3$, $CF_3$, $CO_2H$, and —$CO_2(C_1$-$C_6$ alkyl); $X^1$ is CH; and $X^2$ is CH.

Another embodiment comprises compounds of Formula V, or a pharmaceutically acceptable salt thereof, wherein $R_7$ is selected from the group of H, F, Cl, $CH_3$, $CF_3$, $CO_2H$, and —$CO_2(C_1$-$C_6$ alkyl); $X^1$ is N; and $X^2$ is CH.

A further embodiment comprises compounds of Formula V, or a pharmaceutically acceptable salt thereof, wherein $R_7$ is selected from the group of H, F, Cl, $CH_3$, $CF_3$, $CO_2H$, and —$CO_2(C_1$-$C_6$ alkyl); $X^1$ is CH; and $X^2$ is N.

A separate embodiment comprises compounds of Formula V, or a pharmaceutically acceptable salt thereof, wherein $R_7$ is selected from the group of F, Cl, $CH_3$, and $CF_3$; $X^1$ is CH; and $X^2$ is CH.

Another embodiment comprises compounds of Formula V, or a pharmaceutically acceptable salt thereof, wherein $R_7$ is selected from the group of F, Cl, $CH_3$, and $CF_3$; $X^1$ is N; and $X^2$ is CH.

A further embodiment comprises compounds of Formula V, or a pharmaceutically acceptable salt thereof, wherein $R_7$ is selected from the group of F, Cl, $CH_3$, and $CF_3$; $X^1$ is CH; and $X^2$ is N.

Also provided is a compound of Formula VI, or a pharmaceutically acceptable salt thereof:

Formula VI wherein:

$R_7$ is selected from the group of H, F, Cl, $CH_3$, $CF_3$, $CO_2H$, and $—CO_2(C_1-C_6$ alkyl);

$X^1$ is selected from the group of CH and N; and $X^2$ is selected from the group of CH and N;

with the proviso that only one of $X^1$ and $X^2$ can be N; or a pharmaceutically acceptable salt thereof.

One embodiment comprises compounds of Formula VI, or a pharmaceutically acceptable salt thereof, wherein $R_7$ is selected from the group of H, F, Cl, $CH_3$, $CF_3$, $CO_2H$, and $—CO_2(C_1-C_6$ alkyl); $X^1$ is CH; and $X^2$ is CH.

Another embodiment comprises compounds of Formula VI, or a pharmaceutically acceptable salt thereof, wherein $R_7$ is selected from the group of H, F, Cl, $CH_3$, $CF_3$, $CO_2H$, and $—CO_2(C_1-C_6$ alkyl); $X^1$ is N; and $X^2$ is CH.

A further embodiment comprises compounds of Formula VI, or a pharmaceutically acceptable salt thereof, wherein $R_7$ is selected from the group of H, F, Cl, $CH_3$, $CF_3$, $CO_2H$, and $—CO_2(C_1-C_6$ alkyl); $X^1$ is CH; and $X^2$ is N.

A separate embodiment comprises compounds of Formula VI, or a pharmaceutically acceptable salt thereof, wherein $R_7$ is selected from the group of F, Cl, $CH_3$, and $CF_3$; $X^1$ is CH; and $X^2$ is CH.

Another embodiment comprises compounds of Formula VI, or a pharmaceutically acceptable salt thereof, wherein $R_7$ is selected from the group of F, Cl, $CH_3$, and $CF_3$; $X^1$ is N; and $X^2$ is CH.

A further embodiment comprises compounds of Formula VI, or a pharmaceutically acceptable salt thereof, wherein $R_7$ is selected from the group of F, Cl, $CH_3$, and $CF_3$; $X^1$ is CH; and $X^2$ is N.

Also provided herein is a compound selected from the group of:

Compound 8

6-phenyl-3,4-dihydroisoquinolin-1(2H)-one

Compound 9

6-(3-fluorophenyl)-3,4-dihydroisoquinolin-1(2H)-one

Compound 10

6-(3-chlorophenyl)-3,4-dihydroisoquinolin-1(2H)-one

Compound 11

6-(m-tolyl)-3,4-dihydroisoquinolin-1(2H)-one

Compound 12

6-(3-(trifluoromethyl)phenyl)-3,4-dihydroisoquinolin-1(2H)-one

Compound 13

3-(1-oxo-1,2,3,4-tetrahydroisoquinolin-6-yl)benzoic acid

Compound 14

5-methyl-6-phenyl-3,4-dihydroisoquinolin-1(2H)-one

-continued

Compound 15

5-methyl-6-(pyridin-3-yl)-3,4-
dihydroisoquinolin-1(2H)-one

Compound 16

5-methyl-6-(pyridin-4-yl)-3,4-
dihydroisoquinolin-1(2H)-one

Compound 17

6-(1H-indol-5-yl)-5-methyl-3,4-
dihydroisoquinolin-1(2H)-one

Compound 18

5-methyl-6-(1H-pyrrolo[2,3-b]pyridin-5-yl)-
3,4-dihydroisoquinolin-1(2H)-one

Compound 19

5-methyl-6-(quinolin-3-yl)-3,4-
dihydroisoquinolin-1(2H)-one

-continued

Compound 20

6-(2-fluoropyridin-4-yl)-5-methyl-3,4-
dihydroisoquinolin-1(2H)-one

Compound 21

6-(2-chloropyridin-4-yl)-5-methyl-
3,4-dihydroisoquinolin-1(2H)-one

Compound 22

5-methyl-6-(2-(trifluoromethyl)pyridin-4-yl)-
3,4-dihydroisoquinolin-1(2H)-one Compound 23 and 6-(5-fluoropyridin-3-yl)-5-methyl-
3,4-dihydroisoquinolin-1(2H)-one

Compound 24

5-methyl-6-(trifluoromethyl)pyridin-3-yl)-
3,4-dihydroisoquinolin-1(2H)-one or a pharmaceutically acceptable salt thereof.

Also described for a compound of Formulas I, II, III, IV, V, and VI, as well as the individual compounds disclosed herein, are the pharmaceutically acceptable salts, pharmaceutically acceptable co-crystals, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs of such compounds.

The compounds of the disclosure may possess an asymmetric center, and can be produced as a racemic mixture or as individual enantiomers. The individual enantiomers may be obtained by asymmetric synthesis or by resolving a racemic or non-racemic mixture of an intermediate at some appropriate stage of the synthesis. The individual enantiomers may also be obtained by resolution of the compound by conventional means, such as crystallization in the presence of a resolving agent, or chromatography, using, for example a chiral high-pressure liquid chromatography (HPLC) column. The individual enantiomers as well as racemic and non-racemic mixtures of enantiomers are within the scope of the present disclosure, all of which are intended to be included within the structures depicted in this specification unless otherwise specifically indicated.

Definitions

The term "alkyl" refers to a straight or branched hydrocarbon. For example, an alkyl group can have 1 to 20 carbon atoms (i.e., $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

The term "alkoxy" refers to a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

The term "alkenyl" refers to a straight or branched hydrocarbon with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2CH$=$CH_2$), cyclopentenyl (—$C_5H_7$), and 5-hexenyl (—$CH_2CH_2CH_2CH_2CH$=$CH_2$).

The term "alkynyl" refers to a straight or branched hydrocarbon with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargylic (—$CH_2C$≡CH), and the like.

The term "heterocycle" or "heterocyclyl" as used herein includes by way of example and not limitation those heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g., 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, .beta.-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or .beta.-carboline. Still more typically, nitrogen bonded heterocycles include 1-aziridyl, 1-azetedyl, 1-pyrrolyl, 1-imidazolyl, 1-pyrazolyl, and 1-piperidinyl.

It is understood that, unless otherwise indicated, the ring structures in Formulas I, II, III, IV, V, and VI may be bound to the 3,4-Dihydroisoquinoline-1(2H)-one core through any available ring atom. For instance, the general attachment of naphthalenyl and indolyl groups at $R_1$ could be indicated as shown below:

The term "cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 7 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or spiro. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, bicyclo [3.1.0]hex-6-yl and the like.

"Pharmaceutically acceptable salts", as used herein, includes, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesuflonate (besylate), p-toluenesulfonate (tosylate), 2-hydroxyethylsulfonate, benzoate, salicylate, stearate, and alkanoate (such as acetate, HOOC—$(CH_2)_n$—COOH where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

Also provided herein are pharmaceutical compositions comprising a pharmaceutically effective amount of a compound described herein, or a pharmaceutically acceptable salt thereof, and a pharmaceutically acceptable carrier.

The terms "therapeutically effective amount" or "pharmaceutically effective amount" refers to an amount that is sufficient to effect treatment, as defined below, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art. For example, a "therapeutically effective amount" or a "pharmaceutically effective amount" of a compound of Formula I (including those of Formulas II, III, IV, V, and VI), or a pharmaceutically acceptable salt or co-crystal thereof, is an amount sufficient to modulate the activity in question, and thereby treat a subject (e.g., a human) suffering an indication, or to ameliorate or alleviate the existing symptoms of the indication. For example, a therapeutically or pharmaceutically effective amount may be an amount sufficient to decrease a symptom of a disease or condition responsive to inhibition of PARP10 or PARP16 activity.

A pharmaceutically effective amount of a compound herein may be determined by a medical practitioner. Ranges of pharmaceutically effective amounts of the compounds herein include from about 0.1 mg to about 1,000 mg, from about 1 mg to about 500 mg, from about 1 mg to about 400 mg, from about 1 mg to about 300 mg, from about 1 mg to about 200 mg, from about 1 mg to about 100 mg, from about 1 mg to about 50 mg, from about 50 mg to about 100 mg, from about 100 mg to about 200 mg, from about 100 mg to about 500 mg, and from about 500 mg to about 1,000 mg per dose.

The compounds and pharmaceutical compositions described herein may be used in the treatment of conditions In one embodiment of the first aspect, the ER stress-related condition is a cancer, protein folding/misfolding disease, diabetes mellitus, Wolcott-Rallison syndrome, ischemia/reperfusion injury, stroke, neurodegeneration, atherosclerosis, neoplasia, hypoxia, or hypoglycemia. Cancers which may be treated with compounds herein includes colon adenocarcinoma, esophagus adenocarcinoma, liver hepatocellular carcinoma, squamous cell carcinoma, pancreas adenocarcinoma, islet cell tumor, rectum adenocarcinoma, gastrointestinal stromal tumor, stomach adenocarcinoma, adrenal cortical carcinoma, follicular carcinoma, papillary carcinoma, breast cancer, ductal carcinoma, lobular carcinoma, intraductal carcinoma, mucinous carcinoma, Phyllodes tumor, Ewing's sarcoma, ovarian adenocarcinoma, endometrium adenocarcinoma, granulose cell tumor, mucinous cystadenocarcinoma, cervix adenocarcinoma, vulva squamous cell carcinoma, basal cell carcinoma, prostate adenocarcinoma, giant cell tumor of bone, bone osteosarcoma, larynx carcinoma, lung adenocarcinoma, kidney carcinoma, urinary bladder carcinoma, Wilm's tumor, and lymphoma. Protein folding/misfolding diseases include Huntington's disease, spinobulbar muscular atrophy (Kennedy disease), Machado-Joseph disease, dentatorubral-pallidoluysian atrophy (Haw River Syndrome), spinocerebellar ataxia, Alzheimer's disease, Parkinson's disease, amyotrophic lateral sclerosis (ALS), Creutzfeldt-Jakob disease, bovine spongiform encephalopathy (BSE), light chain amyloidosis (AL), heavy chain amyloidosis (AH), secondary amyloidosis (AA), aortic medial amyloidosis, ApoA1, ApoAII, ad ApoAIV amyloidosis, insulin amyloidosis, cerebral β-amyloid angiopathy, retinal ganglion cell degeneration in glaucoma, prion diseases, cataracts, tauopathies, frontotemporal lobar degeneration (FLTD), FTLD-FUS, amyotrophic lateral sclerosis (ALS/Lou Gehrig's disease), cerebral autosomal dominant arteriopathy with subcortical infarcts and leukoencephalopathy (CADASIL), Alexander disease, familial amyloidotic neuropathy, senile systemic amyloidosis, serpinopthies, Cystic Fibrosis, and Sickle Cell Disease.

Provided herein is a method of treatment of a disease selected from the group above, the method comprising administering to a human in need thereof a pharmaceutically effective amount of a compound of Formula I, or a pharmaceutically acceptable salt thereof. Additional methods for treatment of these diseases comprise administration to the human in need thereof a compound of Formula II, Formula III, Formula IV, Formula V, Formula VI, or an individual compound herein, or a pharmaceutically acceptable salt thereof. The compound of this invention may be administered alone or in combination with other PARP inhibitors, such as small molecule inhibitors or antibodies. For all methods and uses described herein comprising the use of a compound of Formula I, or a pharmaceutically acceptable salt thereof, it is understood that comparable methods or uses are provided using, respectively, a compound of Formula II, Formula III, Formula IV, Formula V, Formula VI, and the individual compounds described herein, or a pharmaceutically acceptable salt thereof.

Additionally provided herein is the use of a compound of any of Formula I, Formula II, Formula III, Formula IV, Formula V, Formula VI, or a pharmaceutically acceptable salt thereof, in the preparation of a medicament. Additional embodiments comprise the use of a compound of any of Formula I, Formula II, Formula III, Formula IV, Formula V, Formula VI, or a pharmaceutically acceptable salt thereof, in the preparation of a medicament for treating each of the diseases or disorders described herein.

Provided herein is a method of sensitizing a cell, such as a cancer cell, to a DNA-damaging agent, the method comprising administering to a human in need thereof a pharmaceutically effective amount of a compound as described herein, or a pharmaceutically acceptable salt thereof.

Also provided is a method of treating a protein folding or a protein misfolding disease in a human, the method comprising administering to a human in need thereof a pharmaceutically effective amount of a compound of Formula I, or a pharmaceutically acceptable salt thereof.

DNA damaging agents will be known by those skilled in the art. Examples of chemotherapeutic DNA damaging agents include cisplatin, carboplatin, oxaliplatin, picoplatin, dicycloplatin, eptaplatin, lobaplatin, miriplatin, nedaplatin, satraplatin, triplatin tetranitrate, doxorubicin, daunorubicin, epirubicin, idarubicin, procarbazine, altretamine, radiotherapy and radiomimetics, such as bleomycin, monofunctional alkylators, including alkylsulphonates, nitrosorosourea compounds (carmustine, lomustine, streptozocin, and semustine), temozolomide, Antimetabolites (5-fluorouracil, capecitabine, floxuridine, gemcitabine, 6-mercaptopurine, 8-azaguanine, fludarabine, cladribine, methotrexate, aminopterin, and pemetrexed), thiopurines, and folate analogues and antifolates (ralitrexed), topoisomerase inhibitors such as camptothecins and etoposide, replication inhibitors such as aphidicoliin and hydroxyurea, calicheamicins and calicheamicin-derived antibody-drug conjugates (ADCs, such as Inotuzumab ozogamicin), and nitrogen mustards (cyclophosphamide, chlormethine, Melphalan, Chlorambucil, Ifosfamide, Bendamustine).

Provided herein is a method of enhancing the function of a DNA damaging agent in a human in need thereof, the method comprising administering to the human a pharmaceutically effective amount of a compound of Formula I, or a pharmaceutically acceptable salt thereof. Comparable methods of enhancing the function of a DNA damaging agent include the use, respectively, of a compound of Formula II, Formula III, Formula IV, Formula V, Formula VI, or any of the specific compounds described herein, or a pharmaceutically acceptable salt thereof. In one embodiment, the compound of this invention is administered simultaneously with the DNA damaging agent. In other embodiments, the compound of this invention is administered subsequently to the DNA damaging agent. For example, the compound of this invention may be administered at a time of 10 minutes, 20 minutes, 30 minutes, 45 minutes, 1 hour, 1 hour and a half, 2 hours, 2 and a half hours, 3 hours, 3 and a half hours, 4 hours, 4 and a half hours, 5 hours, 5 and a half hours, 6 hours, 6 and a half hours, 7 hours, 7 and a half hours, 8 hours, etc., following the administration of the DNA damaging agent. In other embodiments, the compound is administered prior to the DNA damaging agent, including at time periods of the lengths just listed for subsequent administration.

Also provided is a method of treating a subject, such as a human subject, with an ER stress-related condition, the method comprising administering to the human in need thereof a pharmaceutically effective amount of a compound of Formula I, or a pharmaceutically acceptable salt thereof. Separate embodiments also provide for the treatment of an ER stress-related condition in a human comprising, separately, administering to the human in need thereof a pharmaceutically effective amount of a compound Formula II, Formula III, Formula IV, Formula V, or Formula VI, or a pharmaceutically acceptable salt thereof.

Further provided is a method of regulating the unfolded protein response (UPR) of the endoplasmic reticulum (ER) in a human, the method comprising administering to a human in need thereof a pharmaceutically effective amount of a compound of Formula I, or a pharmaceutically acceptable salt thereof.

Compounds of Formula I, Formula II, Formula III, and Formula IV, Formula V, Formula VI, or a pharmaceutically acceptable salt or co-crystal thereof, are usually administered in the form of pharmaceutical compositions. This disclosure therefore provides pharmaceutical compositions that contain, as the active ingredient, one or more of the compounds described, or a pharmaceutically acceptable salt, pharmaceutically acceptable co-crystal or pharmaceutically acceptable ester thereof, and one or more pharmaceutically acceptable vehicle, such as excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compound of Formula I (including those of Formulas II, III, IV, V, and VI), or a pharmaceutically acceptable salt or co-crystal thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In some embodiments, for parenteral administration, sterile injectable solutions are prepared containing a therapeutically effective amount, e.g., 0.1 to 1000 mg, of the compound of Formula I (including those of Formulas II, III, IV, V, and VI), or a pharmaceutically acceptable salt or co-crystal thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

Oral administration is another route for administration of the compound of Formula I (including those of Formulas II, III, IV, V, and VI), or a pharmaceutically acceptable salt or co-crystal thereof. Administration may be via capsule or enteric-coated tablets, or the like. In making the pharmaceutical compositions that include the compound of Formula I (including those of Formulas II, III, IV, V, and VI), or a pharmaceutically acceptable salt or co-crystal thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions as described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient is mixed with a pharmaceutical excipient to form a solid pre-formulation composition containing a homogeneous mixture of the compound of Formula I (including those of Formulas II, III, IV, V, and VI), or a pharmaceutically acceptable salt or co-crystal thereof. When referring to these pre-formulation compositions as homogeneous, it is meant that the active ingredient is dispersed evenly throughout the composition so that the composition may be readily subdivided into equally effective unit dosage forms such as tablets, pills and capsules.

The tablets or pills as described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

For any of the dosage units as described herein, it will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Also provided herein are compounds of Formulas I, II, III, IV, V, and VI that are useful as research tools as selective inhibitors of PARP10 (also known as ARTD10) and PARP 16 (also known as ARTD15). As such, the compounds described herein may be used as comparators for such activity or in the study of biology associated with such inhibition.

We profiled OUL35 against a panel of PARPs for its ability to inhibit the ADP-ribosylation of the promiscuous PARP substrate SRSF protein kinase 2 (SRPK2){Morgan et al., Bioorg. Med. Chem. Lett. 25, 4770-4773; Venkannagari et al., Eur J Pharm Sci, 49, pp. 148-156} using NAD$^+$ (100 µM). In our hands, OUL35 exhibits only 2-fold greater potency for PARP10 in comparison to PARP11 (Table 1). This prompted us to develop a small-molecule chemical probe that demonstrates greater selectivity for PARP10 to aid future studies of PARP10 biology without confounding results due to inhibition of other PARP family members (e.g., PARP11).

TABLE 1

In vitro IC$_{50}$ values for selected 5- and 6-substituted dq compounds against PARP10$_{cat}$ and PARP11

| ID | —R$_5$ | —R$_6$ | PARP10$_{cat}$ IC$_{50}$ (μM) | pIC$_{50}$ ± S.E.M. | PARP11 IC$_{50}$ (μM) | pIC$_{50}$ ± S.E.M. | PARP11/PARP10 |
|---|---|---|---|---|---|---|---|
| OUL35 | — | — | 1.3 | 5.88 ± 0.02 | 2.1 | 5.68 ± 0.03 | 1.6 |
| 1 | H | H | 70.3 | 4.15 ± 0.03 | 8.0 | 5.10 ± 0.04 | 0.11 |
| 2 | Br | H | 10.1 | 4.99 ± 0.04 | 2.9 | 5.54 ± 0.04 | 0.29 |
| 3 | Me | H | 8.6 | 5.01 ± 0.03 | 2.1 | 5.67 ± 0.05 | 0.24 |
| 4 | Ph | H | 35.0 | 4.46 ± 0.04 | 1.2 | 5.93 ± 0.04 | 0.03 |
| 5 | H | Br | 17.1 | 4.77 ± 0.03 | 13.5 | 4.87 ± 0.03 | 0.79 |
| 6 | H | Me | 33.1 | 4.48 ± 0.04 | 34.1 | 4.47 ± 0.06 | 1.0 |
| 7 | H | Bn | >50 | — | 16.7 | 4.78 ± 0.03 | <0.33 |
| 8 | H | Ph | 2.5 | 5.61 ± 0.03 | 8.7 | 5.06 ± 0.03 | 3.5 |
| 9 | H | 3-F—Ph | 1.4 | 5.85 ± 0.03 | 6.1 | 5.22 ± 0.04 | 4.4 |
| 10 | H | 3-Cl—Ph | 1.1 | 5.95 ± 0.02 | 5.8 | 5.24 ± 0.03 | 5.3 |
| 11 | H | 3-Me—Ph | 2.1 | 5.67 ± 0.02 | 4.6 | 5.34 ± 0.03 | 2.2 |
| 12 | H | 3-CF$_3$—Ph | 2.3 | 5.65 ± 0.03 | 17.4 | 4.76 ± 0.04 | 7.6 |
| 13 | H | 3-Ac—Ph | 1.6 | 5.81 ± 0.04 | 4.9 | 5.31 ± 0.05 | 3.1 |
| 14 | Me | Ph | 1.6 | 5.80 ± 0.03 | 26.4 | 4.58 ± 0.07 | 17 |
| 15 | Me |  | 2.5 | 5.60 ± 0.04 | 30.4 | 4.52 ± 0.06 | 12 |
| 16 | Me |  | 1.4 | 5.84 ± 0.03 | 21.2 | 4.67 ± 0.04 | 15 |
| 17 | Me |  | 1.1 | 5.96 ± 0.03 | 4.2 | 5.38 ± 0.04 | 3.8 |
| 18 | Me |  | 0.71 | 6.15 ± 0.03 | 12.0 | 4.92 ± 0.05 | 17 |
| 19 | Me |  | 1.8 | 5.75 ± 0.02 | 14.0 | 4.86 ± 0.04 | 7.8 |

Figure 1B:
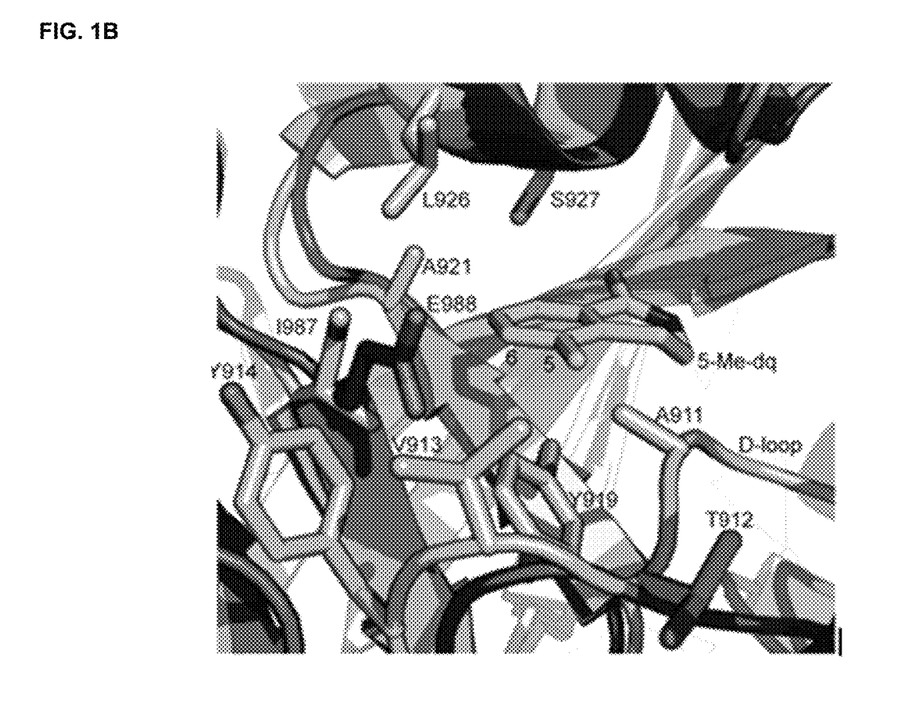
FIG. 1B depicts the structure of PARP10 overlaid with cocrystal structure of PARP1 and 5-methyl-dq.

The 3,4-dihydroisoquinolin-1(2H)-one (dq, 1; FIG. 1A) scaffold has been utilized in the development of inhibitors for PARP1. {Ferraris et al., Eur. J. Med., 2010, Chem. 95, pp. 546-551; Suto et al., Anticancer Drug Des., 1991, 6, 107-117} We showed previously that 1 can be modified to inhibit PARP10 using a chemical genetics strategy {Morgan: 2015jg} and reasoned that 1 would be a good starting point for optimizing an inhibitor with increased selectivity for PARP10 over PARP11. We analyzed the structure of PARP10 overlaid with the cocrystal structure of PARP1 and 5-methyl-dq (3) and hypothesized that modifications on the 5- and 6-position of the dq scaffold could interact with a hydrophobic pocket in PARP10 surrounded by residue 1987 and D-loop residues Y914, V913, and A911 (FIG. 1B). The D-loop is one of the regions of high sequence variability among the PARP family {Pinto et al., 2015, Microbiol. Immunol, 384, pp. 153-166}. We proposed that targeting this region for inhibitor development could impart selectivity for PARP10 over PARP11.

FIG. 2 depicts rational design of a selective inhibitor of PARP10 based on a 3,4-dihydroisoquinolin-1(2H)-one scaffold. FIG. 1A shows the structure of previously reported PARP10-selective inhibitor OUL35. {Venkannagari et al., 2016, Cell Chem. Biol. 23, pp. 1251-1260} and 3,4-dihydroisoquinolin-1(2H)-one (dq, 1) scaffold with 5- and 6-positions indicated. FIG. 1B shows the structure of PARP10 (PDB ID: 3HKV) overlaid with cocrystal structure of PARP1 and 5-methyl-dq (3) (PDB ID: 1PAX).

In order to determine selectivity for PARP10 over PARP11, a structure-activity relationship (SAR) study was performed with dq compounds substituted at both the 5- and 6-position. The synthesis of the dq scaffold involved either a Schmidt reaction of substituted 1-indanones or an acid-catalyzed cyclization of carbamoyl salicylates of substituted phenethylamines. {Kurouchi et al., 2014, Chemistry, 20, 8682-8690. doi:10.1002/chem.201402447} To introduce aryl modifications on the dq scaffold, a Suzuki reaction of bromo-modified dq compounds was performed using the corresponding trifluoroborate or boronic acid species (Scheme 1 and Supporting Information).

1-one (CAS Reg. No. 863479-18-9), 2,3-dihydro-5-[3-(trifluoromethyl)phenyl]-1H-inden-1-one (CAS Reg. No. 262376-27-2), Synthesis of Aryl-Substituted 3,4-dihydroisoquinolin-1(2H)-ones via Suzuki-Miyaura Cross-Coupling General Method A:

A mixture of an appropriate bromo-modified dq (0.25 mmol), potassium alkyltrifluoroborate (0.375 mmol), Pd(OAc)$_2$ (2.8 mg, 0.0125 mmol), RuPhos (11.7 mg, 0.025 mmol), and Cs$_2$CO$_3$ (244 mg, 0.75 mmol) was suspended in toluene/H$_2$O (3:1, 3 mL) and the mixture was bubbled with Ar for 10 min. The reaction was sealed and heated at 95° C. for 3 h. The reaction was concentrated in vacuo and portioned between DCM/H$_2$O (1:1, 10 mL). The DCM layer was removed. The aqueous layer was further extracted with DCM (2×10 mL). The combined organic layers were dried over Na$_2$SO$_4$, filtered, and concentrated in vacuo. The crude residue was taken up in MeOH/0.1% aqueous formic acid (3:1, 4 mL) and purified via preparatory HPLC. Fractions containing product were pooled and concentrated in vacuo to yield the product.

Scheme 1. Synthesis of 3,4-dihydroisoquinolin-1(2H)-ones with modifications at the 5- and 6- position$^a$ a: $R_1$ = Br, $R_2$ = H
b: $R_1$ = H, $R_2$ = Br
c: $R_1$ = H, $R_2$ = Me
d: $R_3$ = Me, $R_4$ = H
e: $R_3$ = Me, $R_4$ = Br $^a$Conditions: a) NaN$_3$ (1.5 equiv), DCM/MsOH (2:1), 0° C. to rt, 18 h; b) 28 (1.05 equiv), THF, rt, 0.5 h; c) TfOH (10 equiv), DCM, 0° C. to rt over 3 h; d) R—BF$_3$K (1.5 equiv), Pd(OAc)$_2$ (5 mol %), RuPhos (10 mol %), Cs$_2$CO$_3$ (3 equiv), toluene/H$_2$O (3:1), 95° C., 3 h; e) R—B(OH)$_2$, Pd(OAc)$_2$ (1 mol %), TBAB (1 equiv), K$_2$CO$_3$ (10 equiv), H$_2$O, 95° C., 3 h; f) R—B(OH)$_2$, Pd(dppf)Cl$_2$·CH$_2$Cl$_2$ (5 mol %), aq. K$_2$CO$_3$ (6 equiv), toluene/EtOH (3:1), 95° C., 3 h.

Examples of starting materials for the reactions of Scheme 1(a) include 2,3-dihydro-5-phenyl-1H-inden-1-one (CAS Reg. No. 185945-75-9), 5-(3-fluorphenyl)-2,3-dihydro-1H-inden-1-one (CAS Reg. No. 863479-19-0), 5-(3-chlorphenyl-2,3-dihydro-1H-inen-1-one (CAS Reg. No. 289619-62-1), 2,3-dihydro-5-(3-methylphenyl)-1H-inden- General Method B:

A mixture of an appropriate bromo-modified dq (0.25 mmol), arylboronic acid (0.275 mmol), K$_2$CO$_3$ (346 mg, 2.50 mmol), tetrabutylammonium bromide (81 mg, 0.25 mmol) was suspended in ddH$_2$O (0.5 mL) under Ar atmosphere. Pd(OAc)$_2$ (0.56 mg, 0.0025 mmol) was added, and the reaction was sealed and warmed to 95° C. for 3 h. After cooling to rt, the reaction mixture was diluted with EtOAc (10 mL), dried over $Na_2SO_4$, filtered, and concentrated in vacuo. The crude residue was purified over a short plug of silica, eluting first with DCM, followed by 20% EtOAc/Hex, and finally with EtOAc to elute product.

General Method C:

A mixture of an appropriate bromo-modified dq (0.125 mmol), arylboronic acid (0.25 mmol), $Pd(dppf)Cl_2.CH_2Cl_2$ (5 mol %), aq. $K_2CO_3$ (0.038 mL, 2M, 0.75 mmol) was suspended in toluene/EtOH (3:1, 2.3 mL) and the mixture was bubbled with Ar for 10 min. The reaction was refluxed at 110° C. under Ar for 3 h. The reaction was concentrated in vacuo and partitioned between $DCM/H_2O$ (1:1, 10 mL). The DCM layer was removed. The aqueous layer was further extracted with DCM (2×10 mL). The combined organic layers were dried over $Na_2SO_4$, filtered, and concentrated in vacuo. The crude residue was taken up in MeOH/0.1% aqueous formic acid (3:1, 4 mL) and purified via preparatory HPLC. Fractions containing product were pooled and concentrated in vacuo to yield the product.

5-methyl-6-phenyl-3,4-dihydroisoquinolin-1(2H)-one (14)

Using General Method B from 25 (17 mg, 0.071 mmol) and phenylboronic acid (17 mg, 0.139 mmol), additional purification using preparatory HPLC; yield: 9.6 mg (0.040 mmol, 57%). 1H NMR (400 MHz, DMSO-$d_6$) δ 7.95 (s, 1H), 7.78 (d, J=7.9 Hz, 1H), 7.54-7.43 (m, 2H), 7.42-7.37 (m, 1H), 7.35-7.26 (m, 2H), 7.18 (d, J=7.9 Hz, 1H), 3.41 (td, J=6.6, 2.7 Hz, 2H), 2.89 (t, J=6.6 Hz, 2H), 2.15 (s, 3H); HRMS (ESI+) for $C_{16}H_{15}NO$ [M+H] expected: m/z=238.12264, found: m/z=238.12318.

5-methyl-6-(pyridiny-3-yl)-3,4-dihydroisoquinolin-1(2H)-one (15)

Using General Method C from 25 (30 mg, 0.125 mmol) and 3-pyridinylboronic acid (30.7 mg, 0.250 mmol); yield: 19.7 mg (0.083 mmol, 66%). 1H NMR (400 MHz, DMSO-$d_6$) δ 8.61 (d, J=4.8 Hz, 1H), 8.55 (s, 1H), 8.00 (s, 1H), 7.87-7.73 (m, 2H), 7.50 (dd, J=7.8, 4.8 Hz, 1H), 7.23 (d, J=7.9 Hz, 1H), 3.42 (td, J=6.6, 2.7 Hz, 2H), 2.91 (t, J=6.6 Hz, 2H), 2.16 (s, 3H); HRMS (ESI+) for $C_{15}H_{14}N_2O$ [M+H] expected: m/z=239.11789, found: m/z=239.11837.

5-methyl-6-(pyridiny-4-yl)-3,4-dihydroisoquinolin-1(2H)-one (16)

Using General Method C from 25 (30 mg, 0.125 mmol) and 4-pyridinylboronic acid (30.7 mg, 0.250 mmol); yield: 19.1 mg (0.080 mmol, 64%). 1H NMR (400 MHz, DMSO-$d_6$) δ 8.76-8.53 (m, 2H), 8.01 (s, 1H), 7.82 (d, J=7.9 Hz, 1H), 7.46-7.31 (m, 2H), 7.22 (d, J=8.0 Hz, 1H), 3.41 (td, J=6.7, 2.8 Hz, 2H), 2.91 (t, J=6.6 Hz, 2H), 2.16 (s, 3H); HRMS (ESI+) for $C_{15}H_{14}N_2O$ [M+H] expected: m/z=239.11789, found: m/z=239.11819.

6-(1H-indol-5-yl)-5-methyl-3,4-dihydroisoquinolin-1(2H)-one (17)

Using General Method C from 25 (30 mg, 0.125 mmol) and 5-indolylboronic acid (40.3 mg, 0.250 mmol); yield: 23.7 mg (0.086 mmol, 69%). 1H NMR (400 MHz, DMSO-$d_6$) δ 11.19 (s, 1H), 7.91 (s, 1H), 7.76 (d, J=7.9 Hz, 1H), 7.45 (td, J=4.1, 2.0 Hz, 2H), 7.40 (t, J=2.8 Hz, 1H), 7.21 (d, J=7.9 Hz, 1H), 7.11-6.91 (m, 1H), 6.58-6.37 (m, 1H), 3.42 (td, J=6.6, 2.6 Hz, 2H), 2.90 (t, J=6.6 Hz, 2H), 2.18 (s, 3H); HRMS (ESI+) for $C_{18}H_{16}N_2O$ [M+H] expected: m/z=277.13354, found: m/z=277.13422.

5-methyl-6-(1H-pyrrolo[2,3-b]pyridin-5-yl)-3,4-dihydroisoquinolin-1(2H)-one (18)

Using General Method C from 25 (30 mg, 0.125 mmol) and 1H-pyrrolo[2,3-b]pyridin-5-ylboronic acid (40.5 mg, 0.250 mmol); yield: 23.4 mg (0.084 mmol, 67%). 1H NMR (400 MHz, DMSO-$d_6$) δ 11.77 (s, 1H), 8.15 (d, J=2.1 Hz, 1H), 7.96 (s, 1H), 7.90 (d, J=2.1 Hz, 1H), 7.80 (d, J=7.9 Hz, 1H), 7.54 (dd, J=3.4, 2.5 Hz, 1H), 7.25 (d, J=7.9 Hz, 1H), 6.49 (dd, J=3.4, 1.8 Hz, 1H), 3.42 (td, J=6.6, 2.7 Hz, 2H), 2.92 (t, J=6.6 Hz, 2H), 2.19 (s, 3H); HRMS (ESI+) for $C_{17}H_{15}N_3O$ [M+H] expected: m/z=278.12879, found: m/z=278.12951.

5-methyl-6-(quinolin-3-yl)-3,4-dihydroisoquinolin-1(2H)-one (19)

Using General Method C from 25 (30 mg, 0.125 mmol) and quinolone-3-boronic acid (43.3 mg, 0.250 mmol); yield: 30.9 mg (0.107 mmol, 86%). 1H NMR (400 MHz, DMSO-$d_6$) δ 8.89 (d, J=2.3 Hz, 1H), 8.37 (d, J=2.3 Hz, 1H), 8.15-7.97 (m, 3H), 7.87 (d, J=7.9 Hz, 1H), 7.82 (ddd, J=8.4, 6.7, 1.4 Hz, 1H), 7.72-7.62 (m, 1H), 7.36 (d, J=7.9 Hz, 1H), 3.44 (td, J=6.6, 2.7 Hz, 2H), 2.95 (t, J=6.6 Hz, 2H), 2.22 (s, 4H); HRMS (ESI+) for $C_{19}H_{16}N_2O$ [M+H] expected: m/z=289.13354, found: m/z=289.13444.

6-(2-fluoropyridin-4-yl)-5-methyl-3,4-dihydroisoquinolin-1(2H)-one (20)

Using General Method C from 25 (30 mg, 0.125 mmol) and 2-fluoropyridine-4-boronic acid (35.2 mg, 0.250 mmol); yield: 24.5 mg (0.096 mmol, 77%). 1H NMR (400 MHz, DMSO-$d_6$) δ 8.32 (d, J=5.1 Hz, 1H), 8.04 (s, 1H), 7.83 (d, J=8.0 Hz, 1H), 7.35 (ddd, J=5.2, 2.2, 1.3 Hz, 1H), 7.25 (d, J=8.0 Hz, 1H), 7.21 (d, J=1.6 Hz, 1H), 3.41 (td, J=6.7, 2.7 Hz, 2H), 2.91 (t, J=6.6 Hz, 2H), 2.17 (s, 3H); HRMS (ESI+) for $C_{15}H_{13}FN_2O$ [M+H] expected: m/z=257.10847, found: m/z=257.10901.

6-(2-chloropyridin-4-yl)-5-methyl-3,4-dihydroisoquinolin-1(2H)-one (21)

Using General Method C from 25 (30 mg, 0.125 mmol) and 2-chloropyridine-4-boronic acid (39.3 mg, 0.250 mmol); yield: 17.0 mg (0.062 mmol, 50%). 1H NMR (400 MHz, DMSO-$d_6$) δ 8.49 (dd, J=5.1, 0.7 Hz, 1H), 8.04 (s, 1H), 7.82 (d, J=7.9 Hz, 1H), 7.53 (dd, J=1.5, 0.7 Hz, 1H), 7.42 (dd, J=5.1, 1.5 Hz, 1H), 7.25 (d, J=7.9 Hz, 1H), 3.41 (td, J=6.7, 6.2, 2.4 Hz, 2H), 2.91 (t, J=6.6 Hz, 2H), 2.16 (s, 3H); HRMS (ESI+) for $C_{15}H_{13}ClN_2O$ [M+H] expected: m/z=273.07892, found: m/z=273.07935.

5-methyl-6-(2-(trifluoromethyl)pyridin-4-yl)-3,4-dihydroisoquinolin-1(2H)-one (22)

Using General Method C from 25 (30 mg, 0.125 mmol) and 2-trifluoromethylpyridine-4-boronic acid (47.7 mg, 0.250 mmol); yield: 35.1 mg (0.115 mmol, 92%). 1H NMR (400 MHz, DMSO-$d_6$) δ 8.86 (d, J=5.0 Hz, 1H), 8.06 (s, 1H), 7.89 (s, 1H), 7.85 (d, J=8.0 Hz, 1H), 7.74 (dd, J=5.0, 1.5 Hz, 1H), 7.30 (d, J=7.9 Hz, 1H), 3.42 (td, J=6.6, 2.7 Hz, 2H), 2.92 (t, J=6.6 Hz, 2H), 2.17 (s, 3H); HRMS (ESI+) for $C_{16}H_{13}F_3N_2O$ [M+H] expected: m/z=307.10527, found: m/z=307.10590.

6-(5-fluoropyridin-3-yl)-5-methyl-3,4-dihydroiso-quinolin-1(2H)-one (23)

Using General Method C from 25 (30 mg, 0.125 mmol) and 5-fluoropyridine-3-boronic acid (35.2 mg, 0.250 mmol); yield: 28.5 mg (0.111 mmol, 89%). $^1$H NMR (400 MHz, DMSO-$d_6$) δ 8.63 (d, J=2.7 Hz, 1H), 8.44 (s, 1H), 8.03 (s, 1H), 7.90-7.64 (m, 2H), 7.27 (d, J=7.9 Hz, 1H), 3.41 (td, J=6.7, 2.6 Hz, 2H), 2.91 (t, J=6.6 Hz, 2H), 2.17 (s, 3H); HRMS (ESI+) for $C_{15}H_{13}FN_2O$ [M+H] expected: m/z=257.10847, found: m/z=257.10758.

5-methyl-6-(5-(trifluoromethyl)pyridin-3-yl)-3,4-dihydroisoquinolin-1(2H)-on (24)

Using General Method C from 25 (30 mg, 0.125 mmol) and 3-trifluoromethylpyridine-5-boronic acid (47.7 mg, 0.250 mmol); yield: 33.5 mg (0.109 mmol, 87%). $^1$H NMR (400 MHz, DMSO-$d_6$) δ 9.03 (d, J=2.2 Hz, 1H), 8.88 (d, J=1.5 Hz, 1H), 8.23 (t, J=1.6 Hz, 1H), 8.04 (s, 1H), 7.84 (d, J=8.0 Hz, 1H), 7.31 (d, J=8.0 Hz, 1H), 3.42 (td, J=6.4, 2.4 Hz, 2H), 2.92 (t, J=6.6 Hz, 2H), 2.16 (s, 3H); HRMS (ESI+) for $C_{16}H_{13}F_3N_2O$ [M+H] expected: m/z=307.10527, found: m/z=307.10605.

The compounds were screened for inhibition against PARP10$_{cat}$- and PARP11-mediated ADP-ribosylation of SPRK2 (Table 1) using NAD$^+$ (100 μM). Unsubstituted 1 is 9-fold more selective for PARP11 than PARP10 (IC$_{50}$=8 μM versus 70 μM). Substitutions at the 5-position of 1 increased potency for both PARP10 and PARP11, yet selectivity for PARP11 was still retained. Compound 4 with a phenyl group at the 5-position was the most potent (1.2 μM) and selective (30-fold) for PARP11 among the set of compounds tested. When compared to unsubstituted 1, 6-position modifications increased potency for PARP10 but had no effect or decreased potency for PARP11. In particular, with the addition of a phenyl group at the 6-position (compound 8), potency for PARP10 was increased 28-fold from 1. Compound 8 was also 4-fold more selective for PARP10 over PARP11, suggesting that 8 could serve as a starting point to further increase selectivity for PARP10.

We proposed that modifications on the phenyl ring of compound 8 might further increase the selectivity for PARP10 over PARP11. We began by introducing small substituents at the ortho-, meta-, or para-position. Substituents at the para-position had little effect on the potency of the compounds for both PARP10 and PARP11, while substituents at the ortho-position greatly reduced potency compared to compound 8 (data not shown). However, modifications at the meta-position of the phenyl ring had modest increases in potency for both PARP10 and PARP11 compared to 8 (Table 1) with the exception of the trifluoromethyl-modified compound 12, which showed a 2-fold decrease in potency for PARP11 compared to compound 8. Compound 12, in turn, exhibited the greatest selectivity for PARP10 over PARP11 (8-fold), a 2-fold improvement from parent compound 8. We sought to further increase this observed selectivity for PARP10 over PARP11.

We hypothesized that combining the most promising modifications at both the 5- and 6-position of the dq scaffold could have a synergistic effect of both increasing potency as well as selectivity for PARP10. Compound 3, with a methyl group at the 5-position, resulted in an 8-fold increase in potency for PARP10 compared to unsubstituted 1 (8.6 μM versus 70 μM) (Table 1). Compound 14, with a methyl and phenyl group at the 5- and 6-position, respectively, resulted in a further 5-fold increase in potency for PARP10 compared to 3 (1.6 μM versus 8.6 μM) (Table 1). To our surprise, the selectivity of 14 for PARP10 over PARP11 (17-fold) compared to the selectivity of 3 for PARP10 over PARP11 (0.24-fold) is improved 70-fold by the combination of both the 5-methyl and 6-phenyl modifications in 14. Compound 14 both increased potency and selectivity for PARP10 over PARP11 compared to 3; however, we encountered aqueous solubility issues at higher concentrations when assaying 14. We sought modifications at the 6-position that could maintain the increased selectivity observed with 14 while mitigating any solubility issues.

We therefore turned to the synthesis of compounds with heterocyclic modifications at the 6-position with the potential to increase aqueous solubility. These would be combined with the corresponding methyl group at the 5-position of the dq scaffold (Table 1). We found that pyridin-3-yl (15), pyridin-4-yl (16), and 1H-pyrrolo[2,3-b]pyridin-5-yl (18) modifications at the 6-position in combination with the 5-methyl modification maintained a similar PARP11/PARP10 selectivity ratio as 14 (12-, 15-, and 17-fold, respectively, versus 17-fold). Both 1H-indol-5-yl (17) and quinolin-3-yl (19) modifications at the 6-position resulted in decreased selectivity compared to 14 (4- and 8-fold versus 17-fold). Compounds 15 and 16 with pyridinyl modifications at the 6-position exhibited increased solubility compared to 14 and were taken forward for further optimization.

TABLE 2

In vitro IC$_{50}$ values for 20-24 against PARP10$_{cat}$ and PARP11

| ID | —R$_2$ | —R$_5$ | PARP10$_{cat}$ IC$_{50}$ (μM) | PARP10$_{cat}$ pIC$_{50}$ ± S.E.M. | PARP11 IC$_{50}$ (μM) | PARP11 pIC$_{50}$ ± S.E.M. | PARP11/ PARP10 |
|----|----|----|----|----|----|----|----|
| 16 | H  |     | 1.4 | 5.84 ± 0.03 | 21.2 | 4.67 ± 0.04 | 15 |
| 20 | F  |     | 1.9 | 5.71 ± 0.03 | 44.7 | 4.35 ± 0.05 | 24 |
| 21 | Cl |     | 1.8 | 5.76 ± 0.03 | 27.0 | 4.57 ± 0.02 | 15 |
| 22 | CF$_3$ |  | 1.8 | 5.74 ± 0.02 | 51.7 | 4.29 ± 0.04 | 29 |
| 15 |    | H   | 2.5 | 5.60 ± 0.04 | 30.4 | 4.52 ± 0.06 | 12 |
| 23 |    | F   | 2.2 | 5.66 ± 0.02 | 54.7 | 4.23 ± 0.03 | 25 |
| 24 |    | CF$_3$ | 2.7 | 5.57 ± 0.03 | 92.1 | 4.04 ± 0.03 | 34 |

We first focused our attention on generating a set of compounds based on 16 with halogen modifications at the meta-position of the pyridinyl ring given our results from Table 1. We introduced fluoro, chloro, or trifluoromethyl groups at the 2-position of the pyridin-4-yl group (Table 2). Overall, the introduction of a fluoro group (20) or a trifluoromethyl group (22) increased selectivity almost 2-fold further for PARP10 over PARP11 compared to 16 (24- or 29-fold versus 15-fold). A chloro substituent (21) retained similar selectivity for PARP10 over PARP11. Similar selectivity trends were observed for compounds 23 (—F) and 24 (—CF$_3$) containing the pyridin-3-yl group, increasing selectivity >2-fold for PARP10 over PARP11 compared to 15 (25- or 34-fold versus 12-fold). Compound 24 exhibited the greatest selectivity overall for PARP10 over PARP11 (35-fold); however, compound 22 (29-fold selectivity) was taken forward for cellular testing due to its slightly greater potency for PARP10 (1.8 µM versus 2.7 µM).

Figure 2A:
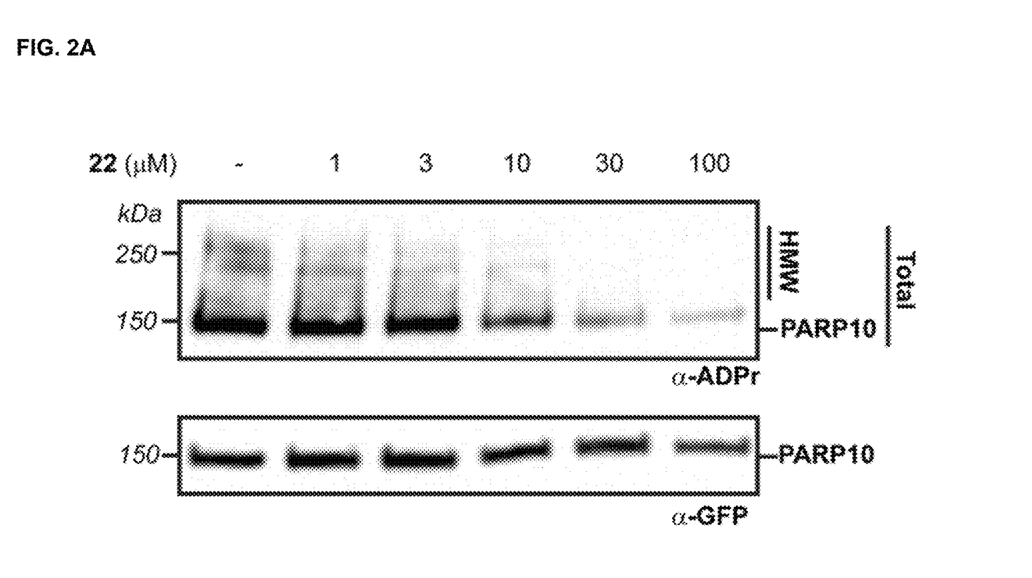
FIG. 2A, represents auto-ADP-ribosylation dose-dependent inhibition of PARP10 by compound 22 in HEK293T cells.
Figure 2B:
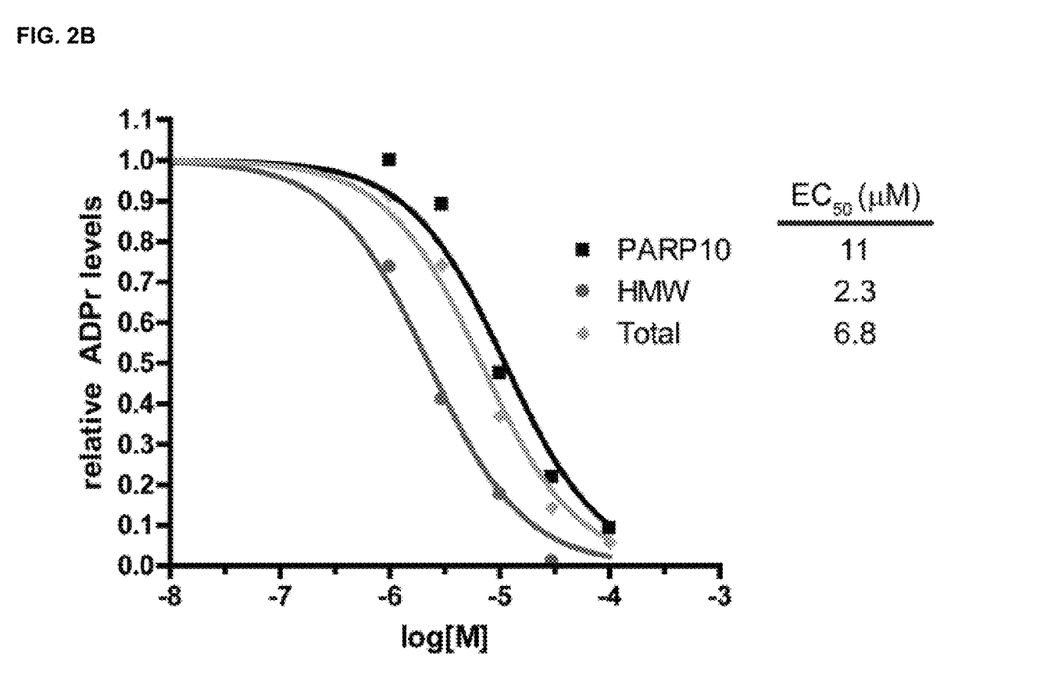
FIG. 2B compares $EC_{50}$ (µM) values quantified for PARP10, itself, and in high molecular weight (HMW) species targets.

We next determined if 22 could inhibit PARP10-dependent ADP-ribosylation in cells. PARP10 is one of the most well-characterized HYφ PARPs and is known to exhibit robust auto-ADP-ribosylation in cells. {Morgan et al., 2015, Bioorg. Med. Chem. Lett. 25, pp. 4770-4773} Human embryonic kidney (HEK) 293T cells expressing full-length PARP10 were treated with increasing concentrations of 22 (1-100 µM). Auto-ADP-ribosylation of PARP10 was monitored by Western blot using an ADP-ribose binding reagent.{Gibson et al., 2016, Science 353, pp. 45-50} We found that 22 inhibits auto-ADP-ribosylation of PARP10 as well as PARP10-labeled targets in a dose-dependent manner (FIG. 2a). The EC$_{50}$ value varies depending on the species quantified. PARP10 targets (HMW species) exhibit a lower EC$_{50}$ compared to PARP10 itself (2.3 µM versus 11 µM) (FIG. 2b), which could be due to the relative stoichiometry differences between the levels of endogenous PARP10 targets and overexpressed PARP10. Both EC$_{50}$ values are in agreement with the in vitro calculated IC$_{50}$ value for 22 against PARP10$_{cat}$ (1.8 µM). These results demonstrate the 22 is membrane permeable and capable of inhibiting auto-ADP-ribosylation of full-length PARP10 and PARP10-modified targets in cells.

Compound 22 inhibits PARP10-dependent ADP-ribosylation in cells as shown in FIG. 2A, which depicts dose-dependent inhibition of PARP10 by 22 in cells. HEK293T cells were transfected with GFP-PARP10 and incubated with increasing concentrations of 22 (1-100 µM) for 3 h. Lysates were prepared and auto-ADP-ribosylation of PARP10 and its high molecular weight (HMW) targets were analyzed with an ADP-ribose binding reagent (α-APDr) (FIG. 2B) Quantification of data shown in FIG. 2(a).

We have shown that 22 is 29-fold more selective for PARP10$_{cat}$ over PARP11 (Table 2). We next wanted to determine the selectivity profile for 22 against a panel of PARP family members.

We screened 22 against poly-ADPr PARPs (PARPs 1, 2, and PARP5b) and mono-ADPr PARPs (PARPs 3, 4, 10, 11, 14, and 15) in an assay that measures ADP-ribosylation of SRPK2 using an N$^6$-alkyne tagged NAD$^+$ (6-a-NAD$^+$), a clickable NAD$^+$ analogue.{Jiang et al., 2010, J. Am. Chem. Soc. 132, 9363-9372; Carter-O'Connell et al., 2014,} (Table 3). Compound 22 does not inhibit PARPs 1-4 and PARP 5b up to 100 µM, exhibiting greater than 37-fold selectivity for PARP10. The observed selectivity is most likely due to the differences in the last position of the H-Y-E catalytic triad of these enzymes versus the H-Y-I triad found in PARP10. {Hottiger et al., 2010, Trends Biochem. Sci. 35, pp. 208-219} The glutamate (E988 in PARP1) in PARPs 1-4 and PARP 5b most likely clash with the pyridiny-4-yl group at the 6-position of 22, while PARP10 contains an isoleucine (1978) at this position that can accommodate this group (FIG. 1B).

TABLE 3

| Enzyme | IC$_{50}$ (µM) | pIC$_{50}$ ± S.E.M. | PARP/PARP10 |
|---|---|---|---|
| PARP1 | >>100 | — | >>37 |
| PARP2 | >100 | — | >37 |
| PARP3 | >>100 | — | >>37 |
| PARP4$_{brct-cat}$ | >100 | — | >37 |
| PARP5b$_{cat}$ | >>100 | — | >>37 |
| PARP6$_S$ | >30 | | >10 |
| PARP6$_L$ | | | |
| PARP7 | | | |
| PARP8 | >30 | | >10 |
| PARP10$_{cat}$ | 2.7 | 5.56 ± 0.06 | 1 |
| PARP11 | 62.9 | 4.20 ± 0.06 | 23 |
| PARP12 | >30 | | >10 |
| PARP14$_{cat\text{-}wwe}$ | 60.5 | 4.22 ± 0.04 | 22 |
| PARP15$_{cat}$ | 62.9 | 4.20 ± 0.05 | 23 |
| PARP16 | — | — | — |

What is claimed:

1. A compound of Formula IV, or a pharmaceutically acceptable salt thereof:

Formula IV wherein:
R$_1$ is selected from the group of —(CH$_2$)$_n{}^1$-phenyl, —(CH$_2$)$_n{}^2$-naphthalenyl, and —(CH$_2$)$_n{}^3$-Het, wherein Het is a 5- to 10-membered heterocyclic group having 1, 2, 3, or 4 ring nitrogen atoms; with each of the R$_1$ phenyl, naphthalenyl, and Het rings of the —(CH$_2$)$_n{}^1$-phenyl, —(CH$_2$)$_n{}^2$-naphthalenyl, and —(CH$_2$)$_n{}^3$-Het groups, respectively, being independently substituted by 0, 1, 2, 3, 4, or 5 substituents selected from C$_1$-C$_6$ alkyl, C$_1$-C$_6$ alkoxy, OH, halogen, CF$_3$, NH$_2$, NH(C$_1$-C$_6$ alkyl), N(C$_1$-C$_6$ alkyl)$_2$, CO$_2$H, —CO$_2$(C$_1$-C$_6$ alkyl), —CO$_2$-phenyl, —CO$_2$-benzyl, —CO$_2$—C$_3$-C$_6$ cycloalkyl, and —CO$_2$—CH$_2$—C$_3$-C$_6$ cycloalkyl; and n$^1$, n$^2$, and n$^3$ are integers independently selected in each instance from 0, 1, 2, and 3.

2. A compound of claim 1, or a pharmaceutically acceptable salt thereof, wherein R$_1$ is selected from the group of phenyl, naphthalenyl, and Het, wherein Het is a 5- to 10-membered heterocyclic group having 1, 2, 3, or 4 ring nitrogen atoms; with each of the R$_1$ phenyl, naphthalenyl, and Het rings being independently substituted by 0, 1, 2, 3, 4, or 5 substituents selected from C$_1$-C$_6$ alkyl, C$_1$-C$_6$ alkoxy, OH, halogen, CF$_3$, NH$_2$, NH(C$_1$-C$_6$ alkyl), N(C$_1$-C$_6$ alkyl)$_2$, CO$_2$H, —CO$_2$(C$_1$-C$_6$ alkyl), —CO$_2$-phenyl, —CO$_2$-benzyl, —CO$_2$—C$_3$-C$_6$ cycloalkyl, and —CO$_2$—CH$_2$—C$_3$-C$_6$ cycloalkyl.

3. A compound of claim 2, or a pharmaceutically acceptable salt thereof, wherein R$_1$ is selected from the group of phenyl, naphthalenyl, benzyl, pyridinyl, pyrrolidinyl, pyrrolyl, imidazolyl, pyrazolyl, 1,2,3-triazolyl, 1,2,4-triazolyl, tetrazolyl, piperazinyl, pyrazinyl, pyrimidinyl, pyridazinyl, 1,2,3-triazinyl, 1,2,4-triazinyl, 1,3,5-triazinyl, indolyl, purinyl, quinolinyl, isoquinolinyl, benzimidazolyl, pyrrolo[2,3- b]pyridinyl; with each of the $R_1$ rings being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl$)_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl.

4. A compound of claim 2, or a pharmaceutically acceptable salt thereof, wherein $R_1$ is selected from the group of phenyl, naphthalenyl, benzyl, quinolinyl, indolyl, pyridinyl, pyrrolo[2,3-b]pyridinyl; with each of the $R_1$ rings being independently substituted by 0, 1, 2, 3, 4, or 5 substituents selected from $C_1$-$C_6$ alkyl, $C_1$-$C_6$ alkoxy, OH, halogen, $CF_3$, $NH_2$, $NH(C_1$-$C_6$ alkyl), $N(C_1$-$C_6$ alkyl$)_2$, $CO_2H$, —$CO_2(C_1$-$C_6$ alkyl), —$CO_2$-phenyl, —$CO_2$-benzyl, —$CO_2$—$C_3$-$C_6$ cycloalkyl, and —$CO_2$—$CH_2$—$C_3$-$C_6$ cycloalkyl.

5. The compound of claim 2 of Formula VI, or a pharmaceutically acceptable salt thereof:

Formula VI wherein:
$R_7$ is selected from the group of H, F, Cl, $CH_3$, $CF_3$, $CO_2H$, and —$CO_2(C_1$-$C_6$ alkyl);
$X^1$ is selected from the group of CH and N; and
$X^2$ is selected from the group of CH and N;
with the proviso that only one of $X^1$ and $X^2$ can be N; or a pharmaceutically acceptable salt thereof.

6. A compound of claim 2 selected from the group of:

or a pharmaceutically acceptable salt thereof.

7. A pharmaceutical composition comprising a pharmaceutically effective amount of a compound of claim 2, a pharmaceutically acceptable salt thereof.

8. The pharmaceutical composition of claim 7, wherein the compound of claim 2 is selected from the group of:

-continued and

9. The compound of claim 5, wherein $X^1$ is N and $X^2$ is CH, or a pharmaceutically acceptable salt thereof.

10. The compound of claim 5, wherein X is CH and $X^2$ is N, or a pharmaceutically acceptable salt thereof.

* * * * *